US010456108B2

(12) United States Patent
Pelissier et al.

(10) Patent No.: US 10,456,108 B2
(45) Date of Patent: Oct. 29, 2019

(54) SYSTEMS AND METHODS FOR AUTOMATIC TIME GAIN COMPENSATION IN A HANDHELD ULTRASOUND IMAGING SYSTEM

(71) Applicant: Clarius Mobile Health Corp., Burnaby (CA)

(72) Inventors: Laurent Pelissier, North Vancouver (CA); Narges Afsham, Coquitlam (CA); Kris Dickie, Vancouver (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 990 days.

(21) Appl. No.: 14/939,993

(22) Filed: Nov. 12, 2015

(65) Prior Publication Data

US 2017/0135672 A1    May 18, 2017

(51) Int. Cl.
*A61B 8/00* (2006.01)
*A61B 8/14* (2006.01)
*A61B 8/08* (2006.01)
*G01S 7/52* (2006.01)

(52) U.S. Cl.
CPC .............. *A61B 8/4427* (2013.01); *A61B 8/14* (2013.01); *A61B 8/5207* (2013.01); *A61B 8/5269* (2013.01); *G01S 7/52033* (2013.01); *G01S 7/5208* (2013.01)

(58) Field of Classification Search
CPC ....... A61B 8/4427; A61B 8/5207; A61B 8/14; A61B 8/5269; G01S 7/52033
See application file for complete search history.

(56) References Cited

U.S. PATENT DOCUMENTS

| 4,662,380 A | 5/1987 | Riley |
| 5,579,768 A | 12/1996 | Klesenski |
| 6,679,844 B2 | 1/2004 | Loftman et al. |
| 7,645,236 B2 | 1/2010 | Simopoulos et al. |
| 8,414,493 B2 | 4/2013 | Derby, Jr. |
| 2003/0187353 A1* | 10/2003 | Ng .......................... A61B 8/467 600/437 |

(Continued)

OTHER PUBLICATIONS tutorialspoint.com, Concept of Pixel, Oct. 24, 2015 (Year: 2015).*

(Continued)

*Primary Examiner* — Bill Thomson
*Assistant Examiner* — Aminah Asghar
(74) *Attorney, Agent, or Firm* — Julian Ho

(57) ABSTRACT

An apparatus and method for automatically calculating and applying time gain compensation in a handheld or hand-carried ultrasonic imaging machine. The apparatus include an autogain unit to calculate the time gain compensation based on a processed ultrasound image. The image is divided into regions, and the image intensity is used to mask regions which satisfy a threshold. Masked regions are used to calculate a gain curve which is then spatially and temporally smoothed. Means are providing for masking entire columns of regions to remove areas where the probe is not in contact. This approach may allow less experienced users to achieve high quality images without the difficult and time-consuming task of manually adjusting the time gain compensation.

15 Claims, 8 Drawing Sheets

(56) References Cited

U.S. PATENT DOCUMENTS

| | | | |
|---|---|---|---|
| 2006/0030775 A1* | 2/2006 | Adams | G01S 7/52033 600/437 |
| 2007/0016024 A1* | 1/2007 | Simopoulos | A61B 8/08 600/437 |
| 2009/0062648 A1* | 3/2009 | Derby, Jr. | A61B 8/00 600/443 |
| 2010/0286527 A1* | 11/2010 | Cannon | A61B 7/04 600/459 |
| 2014/0358005 A1 | 12/2014 | Hiriyannaiah | |
| 2015/0094591 A1 | 4/2015 | Hiriyannaiah | |
| 2016/0081662 A1 | 3/2016 | Denk et al. | |

OTHER PUBLICATIONS

Wayback machine date stamp of: tutorialspoint.com, Concept of Pixel, Oct. 24, 2015 (Year: 2015).*

Natarajan, S. (2001). "Automatic Gain Control for a Small Portable Ultrasound Device", Department of Electrical Engineering and Computer Science, Massachusetts Institute of Technology, Cambridge.

Moshavegh, R. et al., "Automated Hierarchical Time Gain Compensation for In Vivo Ultrasound Imaging", In Medical Imaging 2015: Ultrasonic Imaging and Tomography, J. G. Bosch, & N. Duric (Eds.), Proceedings of SPIE vol. 9419, 941904.

Lee, D., Kim, Y. S., and Ra, J. B., "Automatic time gain compensation and dynamic range control in ultrasound imaging systems", in Medical Imaging 2006: Ultrasonic Imaging and Signal Processing, S. Emelianov & W. Walker (Eds.), Proceedings of SPIE vol. 6147, 614708.

Abstract of Axelsen, M. C. et al. (2010). "Evaluation of automatic time gain compensated in-vivo ultrasound sequences", in Ultrasonics Symposium (IUS), 2010 IEEE, Date of Conference: Oct. 11-14, 2010.

Abstract of Kim, J. H., Lee, Y., Kang, J., and Yoo, Y., "A real-time realization of an automatic dynamic range adjustment method on a smart mobile device for point-of-care ultrasound imaging", in Ultrasonics Symposium (IUS), 2014 IEEE International. Date of Conference: Sep. 3-6, 2014.

Hugfies, D.I. and Duck, F.A., "Automatic Attenuation Compensation for Ultrasonic Imaging", Ultrasound in Medicine and Biology 23(5) 1997: 651-664. World Federation for Ultrasound in Medicine and Biology.

Pye, S.D., Wild, S.R. and McDicken, W.N., "Adaptive Time Gain Compensation for Ultrasonic Imaging", Ultrasound in Medicine and Biology 18(2) 1992: 205-212.

* cited by examiner

FIG. 5A
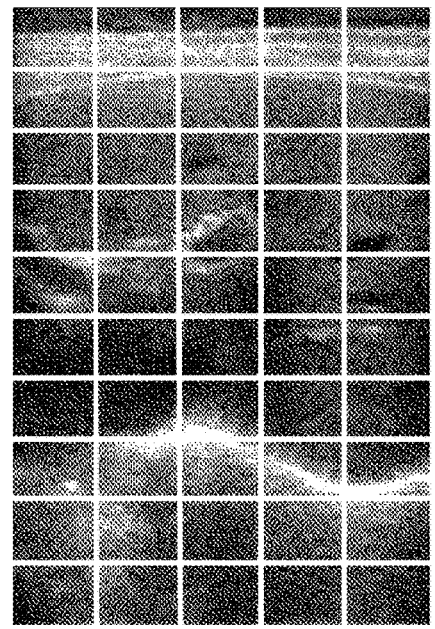
FIG. 5B
| 104 | 122 | 121 | 109 | 107 |
|---|---|---|---|---|
| 100 | 111 | 103 | 91 | 96 |
| 49 | 65 | 65 | 61 | 68 |
| 47 | 69 | 76 | 48 | 53 |
| 60 | 69 | 50 | 33 | 40 |
| 21 | 19 | 20 | 32 | 42 |
| 12 | 21 | 51 | 31 | 31 |
| 62 | 120 | 139 | 109 | 78 |
| 76 | 88 | 48 | 85 | 107 |
| 50 | 60 | 30 | 38 | 41 |
FIG. 5C
| 32 | 37 | 36 | 34 | 33 |
|---|---|---|---|---|
| 31 | 34 | 32 | 29 | 31 |
| 20 | 23 | 23 | 22 | 24 |
| 19 | 24 | 26 | 19 | 21 |
| 22 | 24 | 20 | 16 | 17 |
| 13 | 12 | 13 | 16 | 18 |
| 11 | 13 | 20 | 15 | 15 |
| 23 | 36 | 41 | 34 | 26 |
| 26 | 29 | 19 | 28 | 33 |
| 20 | 22 | 15 | 17 | 18 |
FIG. 5D

| | | | | |
|---|---|---|---|---|
| 32 | 37 | 36 | 34 | 33 |
| 31 | 34 | 32 | 29 | 31 |
| 20 | 23 | 23 | 22 | 24 |
| 19 | 24 | 26 | 19 | 21 |
| 22 | 24 | 20 | 16 | 17 |
| 13 | 12 | 13 | 16 | 18 |
|  | 13 | 20 | 15 | 15 |
| 23 | 36 | 41 | 34 | 26 |
| 26 | 29 | 19 | 28 | 33 |
| 20 | 22 | 15 | 17 | 18 |
FIG. 5E
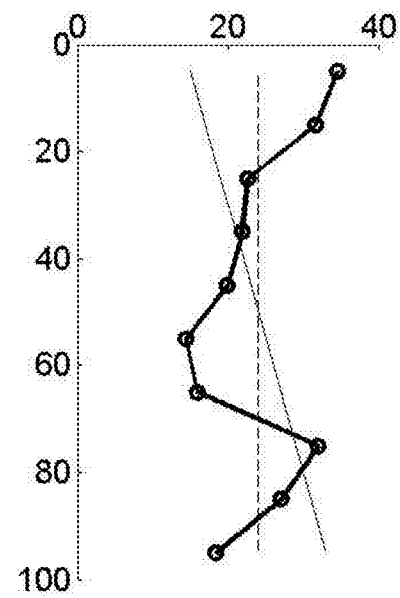
FIG. 5F
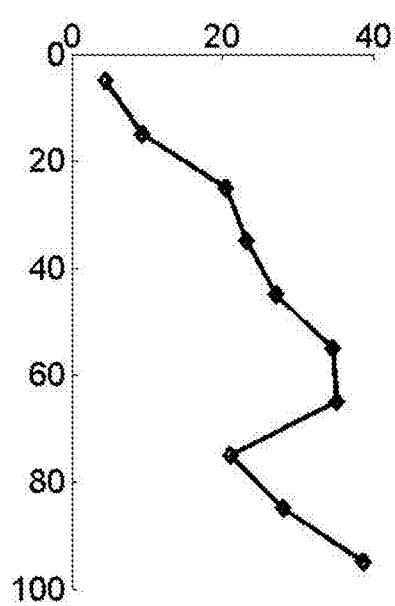
FIG. 5G
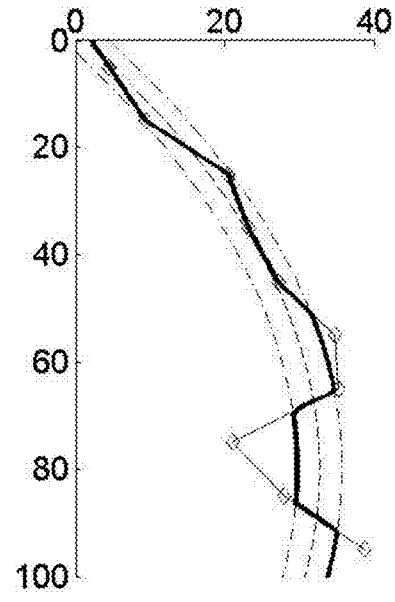
FIG. 5H

SYSTEMS AND METHODS FOR AUTOMATIC TIME GAIN COMPENSATION IN A HANDHELD ULTRASOUND IMAGING SYSTEM

FIELD

This invention relates to ultrasound imaging systems. Embodiments of the invention relate to ultrasound imaging systems that automatically adjust time gain compensation.

BACKGROUND

Ultrasound imaging systems are a powerful tool for performing real-time, non-invasive imaging procedures in a wide range of medical applications. In a typical ultrasound system, a transducer sends out ultrasound signals and receives their echoes. The echoes are processed to produce an ultrasound image of the target anatomy.

The quality of the ultrasound image depends on the skill and experience of the operator. An important and challenging part of acquiring high-quality images is adjusting the various imaging parameters.

Ultrasound waves are attenuated as they propagate deeper into the material being imaged. This results in darker pixels as the depth increases. It is desirable that anatomically identical regions be displayed with the same brightness regardless of depth. Depth-dependent gain, or time gain compensation (TGC), is applied to correct images.

Time gain compensation is further complicated by the fact that the amount of attenuation depends on frequency: higher frequencies are attenuated more than lower frequencies.

Conventional ultrasound systems have large control interfaces with numerous controls which allow operators to adjust a wide range of parameters. For example, time-gain compensation is often adjusted by manually adjusting a number of mechanical sliders that each adjust the gain for a particular depth range. Operators typically rely on trial and error to adjust the gains to produce good images.

There is an increasing demand for small portable ultrasound imaging devices that are still capable of acquiring good quality ultrasound images. Increasing portability and simplicity often involves or requires reducing the number of controls to accommodate smaller screens and smaller devices. Fewer controls and reduced need for manual adjustments also make it easier for new ultrasound operators to learn how to use such smaller devices.

There remains a need for methods and apparatus operable to apply automatic time gain compensation in real time, particularly on simple and/or handheld ultrasonic imaging machines.

SUMMARY

Advantages

Thus several advantages of one or more aspects are to provide systems and methods for automatically adjusting time gain compensation for a handheld ultrasound machine with little or no user intervention. This may make it easier for less experienced operators to achieve a high quality image, enabling better and less expensive diagnosis.

These and other advantages of one or more aspect will become apparent from a consideration of the ensuing description and accompanying drawings.

The description of the invention which follows, together with the accompanying drawings should not be construed as limiting the invention to the examples shown and described, because those skilled in the art to which this invention pertains will be able to devise other forms thereof within the scope of the appended claims.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 5A is an example grayscale ultrasound image.

FIG. 5B is an example grayscale ultrasound image divided into analysis regions.

FIG. 5C is an example matrix of averaged pixel intensities for each analysis region.

FIG. 5D is an example matrix of average pixel intensities for each analysis region transformed into decibels.

FIG. 5E is an example matrix of average pixel intensities for each analysis region of the ultrasound image of FIG. 5A masked with a minimum threshold.

FIG. 5F is an example gain curve with a desired gain level.

FIG. 5G is a graph depicting an example target gain curve.

FIG. 5H is an example target gain curve, a quadratic curve fit to the target gain curve, and upper and lower bounds.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of this invention provides a method for automatically calculating a time gain compensation for an ultrasound imaging machine. The ultrasound imaging machine is hand-held in some embodiments. The invention may also be embodied in apparatus configured to perform automatic time gain compensation as described herein.

Figure 1:
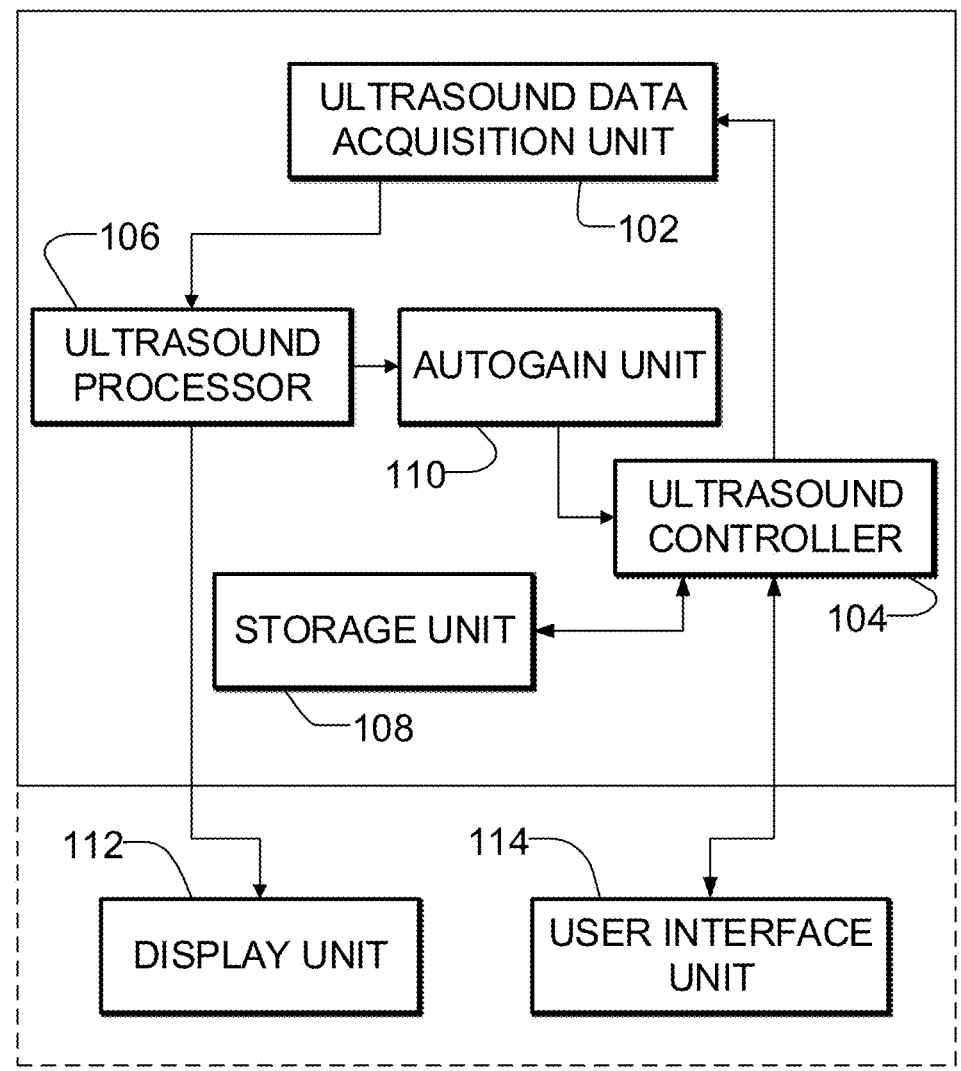
FIG. 1 is a schematic diagram of an ultrasound imaging system according to an example embodiment.

FIG. 1 is a schematic diagram of an example ultrasound imaging system. Ultrasound imaging system 100 comprises an ultrasound data acquisition unit 102 which is coupled to an ultrasound controller 104. Ultrasound controller 104 provides control signals to ultrasound data acquisition unit 102 to direct the transmission of ultrasound pulses and the reception of ultrasound echoes. Signals representing the ultrasound echoes are sent to an ultrasound processor 106 which processes ultrasound echo data into an ultrasound image and transmits the ultrasound image to a display unit 112 for display to a user. Ultrasound controller 104 is also operatively connected to a user interface 104, which allows the user to change settings and interact with the system. Ultrasound controller 104 is also operatively connected to a data store 108 operable to store configurations and settings.

Ultrasound processor 106 may, for example, comprise signal processing circuits (which may include filters, amplifiers and the like) one or more analog to digital converters (ADCs), a beamformer and the like. The principles behind and a wide variety of suitable constructions for ultrasound processor 106 are well understood to those of skill in the art of designing ultrasound machines. Ultrasound data acquisition unit 102 may include a suitable transducer, driving circuits echo signal detection circuits etc. Data acquisition unit 102 includes one or more variable gain amplifiers that apply time-gain compensation to the ultrasound echo signals. The principles behind and a wide variety of suitable constructions for ultrasound data acquisition unit 102 are well understood to those of skill in the art of designing ultrasound machines.

Ultrasound processor 106 is operatively connected to an automatic time-gain compensation (TGC) unit 110. TGC unit 110 is connected to receive ultrasound image data for gain analysis. By analysis of the ultrasound image data, TGC unit 110 automatically calculates a desirable time-gain compensation curve. The curve is provided to ultrasound controller 104 which sets the variable-gain amplifier(s) of ultrasound data acquisition unit 102 to apply the time-gain curve to the ultrasound data. The time-gain curve may be updated in real-time. In some embodiments the time-gain curve is updated after each ultrasound image is acquired.

Figure 2:
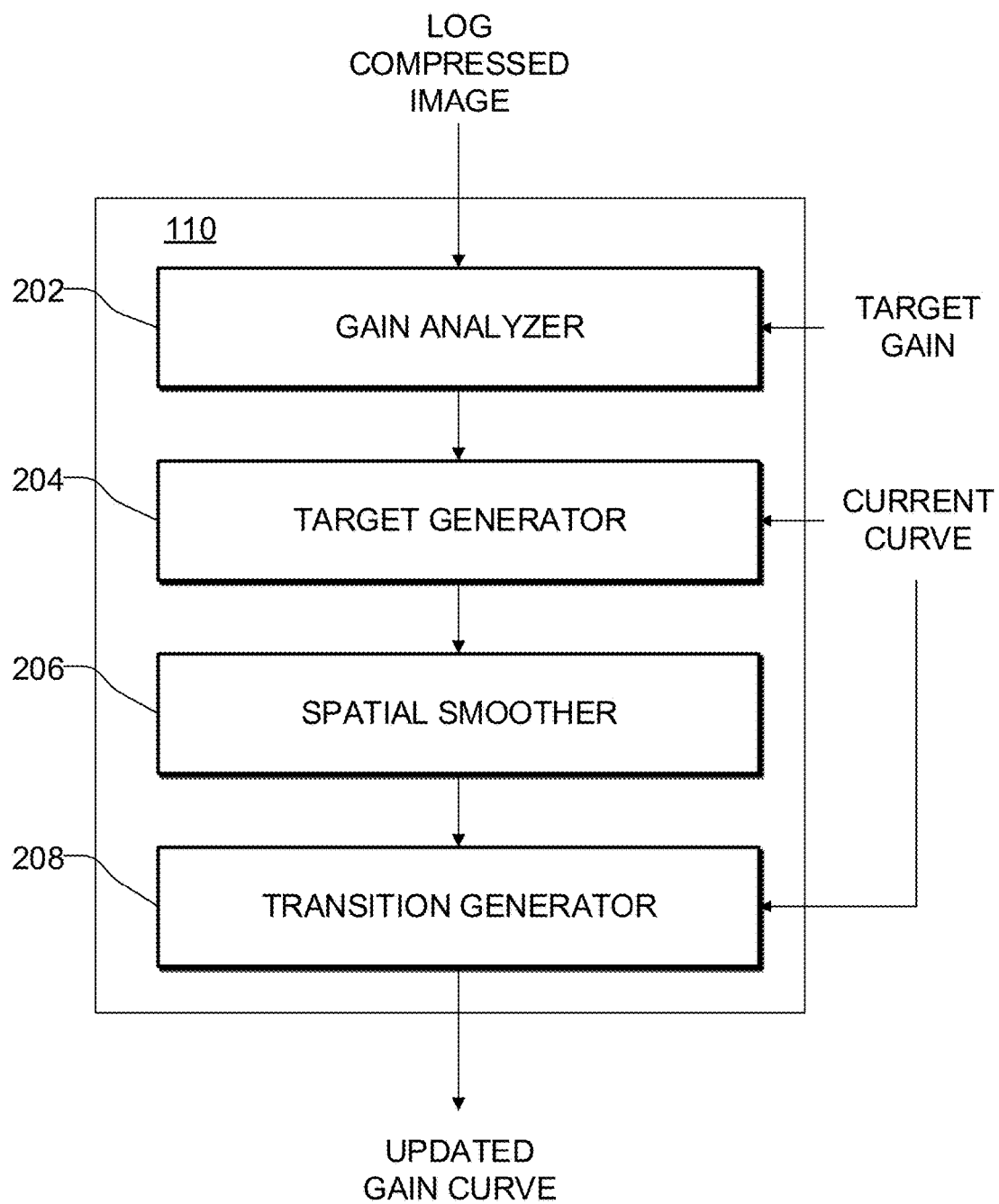
FIG. 2 is a block diagram of an example autogain unit.

FIG. 2 is a schematic diagram illustrating an automatic TGC unit according to one or more aspects of the present disclosure. Automatic TGC unit 110 may comprises several units: a gain analyzer unit 220, a target generator unit 204, a spatial smoother unit 206, and a transition generator unit 208. In other embodiments, the functions of automatic TGC unit 110 may be provided by a different arrangement of subunits. For example, the functions of some or all subunits may be combined.

A typical ultrasound image may be represented by a two-dimensional array comprising multiple lines each comprising multiple samples. The number of lines is typically on the order of one hundred. The number of samples in each line is typically on the order of several hundred. In this description the array may be arranged such that the lines form columns of the array and sets of samples from different lines at the same depth form rows of the array. To produce a single ultrasound image or 'frame', multiple transmit and receive events may be performed.

To improve signal to noise ratio, ultrasound lines are often formed by combining data received at multiple transducer elements. Data received from multiple transducer elements can be combined by using receive beamforming, such as delay and sum beamforming. Multiple lines can be produced for each transmit/receive event by using multiple receive beamformers. Such beamformers may be implemented in ultrasound processor 106 for example.

Once an entire image frame is acquired, the ultrasound data is mapped to a dynamic range suitable for display. It is typically convenient to represent each point or pixel of the ultrasound image by a pixel value or 'greyscale value' in the range of 0-255. The gamut of possible pixel values may include more or fewer than 255 possible values in different embodiments.

Mapping may involve, for example, applying log compression, or a combination of log compression and linear scaling to raw values output by a beamformer.

Gain analyzer unit 202 receives an ultrasound image from ultrasound processor 106 and a target representative pixel value from data store 108 (the target representative pixel value may be fixed or user settable). Gain analyzer 202 processes the ultrasound image data to determine a measure of how pixel values in the ultrasound image tend to vary with depth. Based on this measure, gain analyzer 202 calculates an offset gain curve. The offset gain curve indicates how gain would need to be increased or decreased at different depths to make the measure of how pixel values vary with depth have the desired representative pixel values at different depths.

In some embodiments, the offset gain curve is defined by a number of points. The number of points may be predetermined. The number of points may be changed, for example, by selecting a different imaging preset. Each point corresponds to a specified depth. For each point, the offset gain curve may indicate an amount of change. For example, if a representative pixel value at a depth corresponding to one point of the offset curve is lower than the target representative pixel value then the offset gain curve may specify an increase in gain for that point. If the representative pixel value at a depth corresponding to another point of the offset curve are greater than the target representative pixel value then the offset gain curve may specify an increase in gain for that point. If the representative pixel value at a depth corresponding to still another point of the offset curve is equal to the target representative pixel value then the offset gain curve may specify no change in gain for that point. These amounts of change may be applied to adjust a time-gain compensation being applied by ultrasound processor 106.

Target generator 204 receives the offset gain curve from gain analyzer unit 202 and a current time-gain curve from storage unit 108.

The offset gain curve and the current time-gain curve may be defined by the same or different numbers of points. Interpolation (e.g. linear interpolation) may be applied, if desired to produce an offset gain curve and/or current time-gain curve defined by the same number of points.

The offset gain curve and the current gain curve are combined to produce a rough target gain curve. In some embodiments the offset gain curve (or a multiple of the offset gain curve which, in some embodiments, is a multiple obtained by multiplying by a factor greater than zero and less than one) is added to the current gain curve to yield the rough target gain curve.

Discontinuities in a time-gain curve may result in visual artifacts in the output image, such as horizontal banding. Vertical spatial smoothing is applied to the time-gain curve to reduce abrupt changes that may cause banding. The degree of smoothing may be adjustable. In the illustrated embodiment, spatial smoother unit 206 receives the rough target gain curve from gain analyzer unit 202. Spatial smoother unit 206 smooths the rough target gain curve to produce a target gain curve.

For example, spatial smoother 206 may operate by fitting a curve to the points that define the rough target gain curve. The fit may be, for example a linear fit, a polynomial fit (e.g. a quadratic fit) or another type of fit. In some embodiments different types of fit may be selected by changing imaging presets.

The representative pixel value at different depths is determined not only by the current time-gain compensation curve but also by any structures that may be present in the volume being imaged. The effect of imaged structures on the time-gain curve may be reduced by appropriately calculating the representative values for different depths and also by taking into account the statistics of the distribution of pixel values at different depths in fitting the a curve to the points that define the rough target gain curve.

In an example embodiment, the fitted curve is forced to lie between upper and lower bands. These upper and lower bands may be created based on a statistical metric, for example, the standard deviation of the pixel values in a given row. The fitted curve may be forced to be very close to a point at a depth for which the standard deviation is small. The fitted curve may be allowed to deviate more from points at depths for which the standard deviation is larger.

In another example embodiment, the upper and lower bands may be created based on a predetermined clipping offset from the fitted curve. This predetermined clipping offset may be a constant or may vary with depth. If the rough target gain curve is within the upper and lower bands at a given depth, the value of the rough target gain curve at that depth is used in the target gain curve. If the rough target gain curve is below the lower threshold or above the upper threshold, then the appropriate lower or upper threshold value is used at that depth for the target gain curve. The offset may vary for example from 0-20 dB. With a clipping offset of 0, the target gain curve is the curve fit to the rough target gain curve.

Temporal transition generator unit 208 receives the target time-gain curve from spatial smoother unit 206 and generates a transition time-gain curve to smoothly transition over time from the current time-gain curve to the target gain curve. The transition gain curve may be stored in memory and loaded into an analog gain unit of ultrasound data acquisition unit 102 and/or ultrasound processor 106 to apply gain for the acquisition of the ultrasound echo data for the next frame.

Temporal transition generator unit 208 may use a weighting factor to determine how quickly to transition from the current time-gain curve to the desired target gain curve. This weighting factor may be chosen to trade off the responsiveness of the gain change against the possibility that too-rapid changes in the time-gain curve may cause undesirable visual artifacts.

The weighting factor may be a predetermined constant chosen through testing. Alternatively, the weighting factor may be variable. For example, the weighting factor may be responsive to a measure of motion of a probe that carries the ultrasound transducer. If the probe is moving rapidly then the weighting factor may be set such that the time-gain curve is allowed to change more rapidly. On the other hand, if the probe is not moving or is moving only slowly then the weighting factor may be set such that the time-gain curve is forced to change gradually. For example, a weighting factor of 60% has been experimentally determined to provide a good trade-off between responsiveness and jitter.

Temporal transition generator unit 208 may be configured to not make small unnecessary changes in the time-gain curve. If the differences between the transition time-gain curve and the current time-gain curve are within a deadband, the analog gain unit may continue to use the current time-gain curve. A typical value for the deadband may be 1 dB. The deadband may, for example, be in the range of 0.5 dB to 3 dB.

In one example embodiment, transition generator unit 208 comprises a infinite impulse response (IIR) filter.

The time-gain curve is applied in ultrasound data acquisition unit 102. The time-gain curve may be stored in a memory. Additional TCG hardware may comprise a digital to analog converter (DAC), a filtering unit, an operational amplifier, and individual amplifiers for each receive channel. Digital values from the memory representing the gains to use at different times are input into the DAC. The analog output from the DAC is applied to gain-control inputs of the individual amplifiers. After an ultrasound pulse is transmitted, the TGC controller loads the next TGC value from memory at the appropriate time so that echo signals received during that interval have the correct gain applied.

Operation

Figure 3:
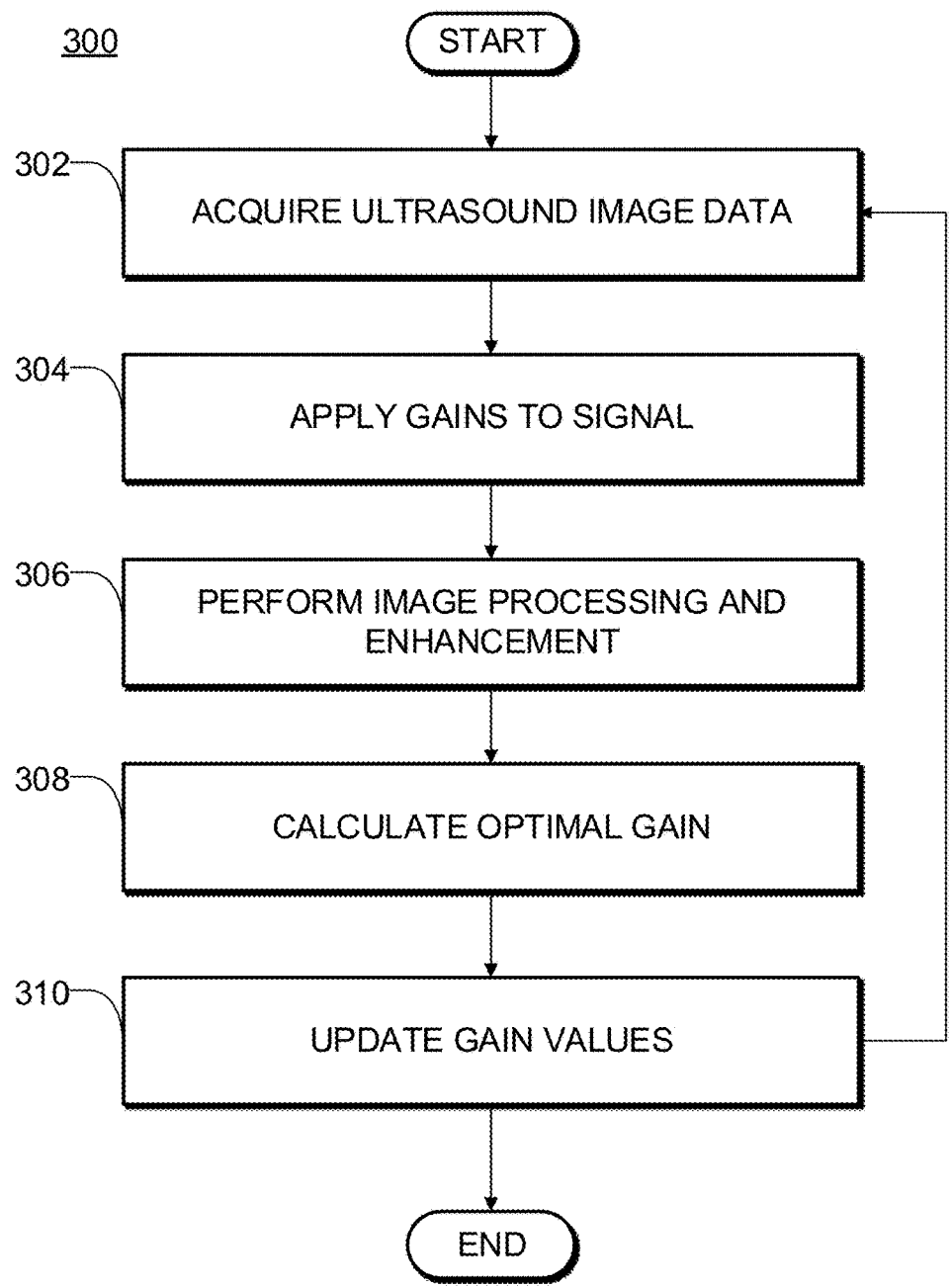
FIG. 3 is a flowchart illustrating an example method for applying an automatically calculated time gain compensation curve.

FIG. 3 illustrates an example method 300 for automatically calculating and applying time-gain compensation in real-time.

In operation 302, ultrasound image data is acquired. Operation 302 involves transmitting ultrasound energy via an ultrasonic transducer and receiving reflected ultrasound energy as ultrasound echoes. The ultrasound echoes are detected at the transducer which outputs corresponding ultrasound echo signals.

In operation 304, the ultrasound echo signals are amplified. The amplification includes applying time-gain compensation according to a current time gain curve. In general, the time-gain compensation causes the amplification to increase with time after transmission of ultrasound energy such that later-received ultrasound echo signals (corresponding to ultrasound that has passed through longer distances in the subject) are amplified more than earlier-received ultrasound echo signals.

In operation 306, the ultrasound data is processed and formed into an ultrasound image. Operation 306 may, for example, comprise receive beamforming.

In operation 308, an autogain algorithm is applied to the ultrasound image to calculate a new TGC gain curve. The autogain algorithm may operate generally as described above, for example.

In operation 310, the new TGC gain is written into memory for the next acquisition cycle.

Figure 4:
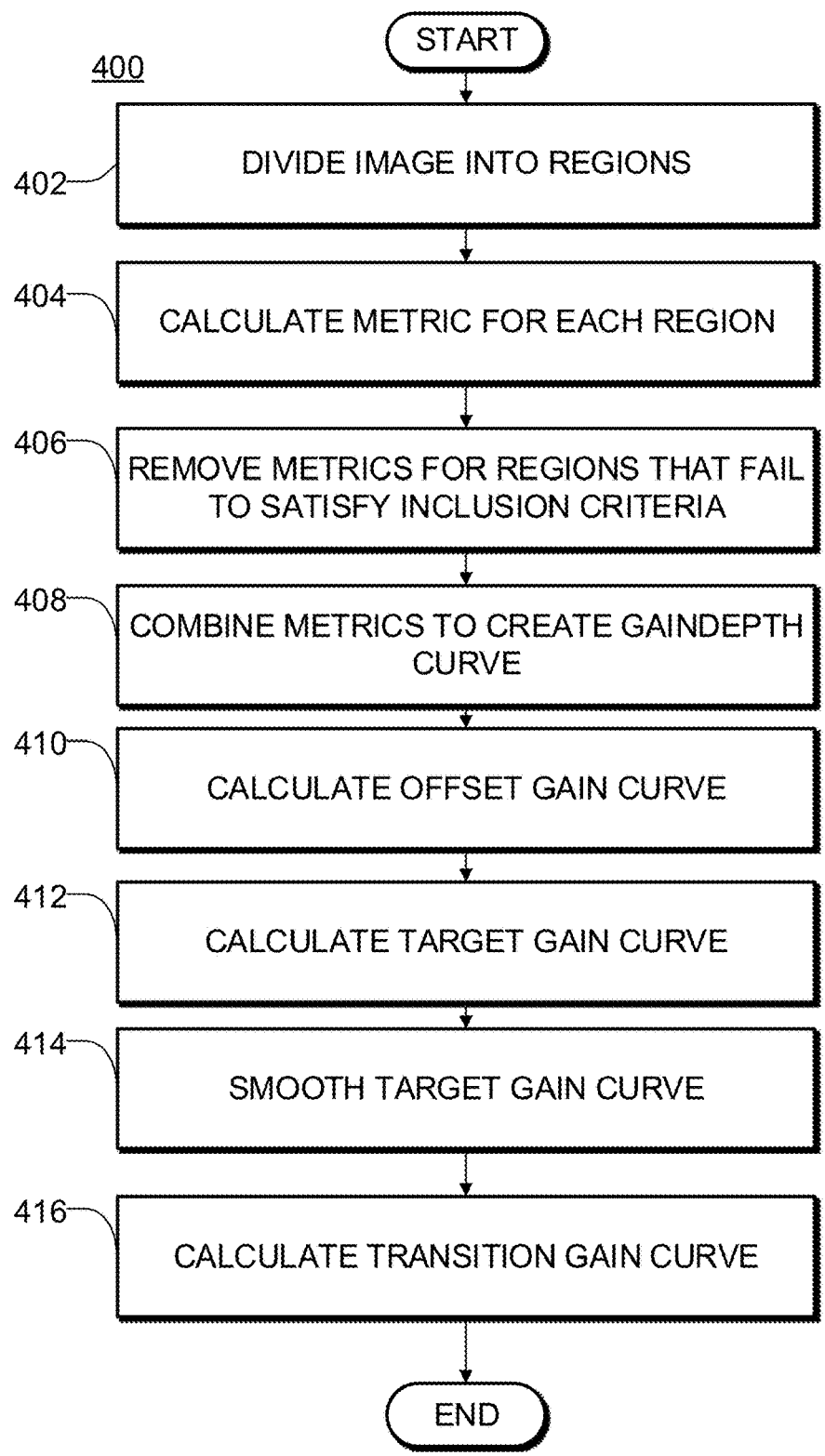
FIG. 4 is a flowchart illustrating an example method for automatically calculating a time gain compensation curve.

FIG. 4 illustrates an example automatic TGC algorithm 400 according to one or more embodiments of the present disclosure.

In operation 402, a grayscale ultrasound image is divided into a number of regions. In some embodiments the regions each comprise a rectangular area of the image. In some embodiments, each row and each column of the array that makes up the image passes through a plurality of the regions. In some embodiments each column (line) of the image passes through three or more of the regions.

There may be a fixed number of regions or the number of regions may be varied depending on imaging depth. For example, the regions may each represent a fixed size that scales with imaging depth.

In operation 404, one or more statistical metrics are calculated for the pixels in each region. The statistical metrics may include a representative value for pixels in the region. The representative value may, for example, comprise an average value, a mean value, or a median value for the pixel values of pixels within the region. In some embodiments extreme pixel values within the region are not included in determining the representative value. For example, a number of the highest and/or lowest pixel values may be excluded from the calculation of the representative value.

The statistical metrics may also include a measure of the range of different pixel values within the region. For example, a standard deviation of the pixel values may be determined. In one example embodiment, the average and standard deviation of pixel values is calculated for each region.

In operation 406, the grayscale ultrasound image is masked based on one or more of the statistical metrics. Masking involves excluding zero or more regions based on criteria relating the statistical metrics. In one example embodiment, any regions whose representative value (e.g. average pixel value) is greater than a masking threshold are masked. The masking threshold may be predetermined based on testing, or may vary depending on an imaging preset.

Masked regions may be said to satisfy an inclusion condition. The inclusion condition in some embodiments may be expressed as: a representative pixel value for a region (which increases with increasing echo strength) is at least equal to a defined threshold.

Non-masked regions are excluded from the calculations. In some embodiments regions for which the statistical metric is between upper and lower thresholds are masked while regions for which the statistical metric is outside the range defined between the thresholds may be excluded from the calculations. In some embodiments the threshold(s) are set to exclude regions having very weak or no ultrasound echoes. In some embodiments the thresholds are also set to exclude regions having anomalously strong ultrasound echoes.

In operation 408, statistical metrics for masked regions are used to calculate an image intensity curve. In one embodiment, a point of the image intensity curve is calculated for each row of regions by averaging the average pixel values for all masked regions in the row. Additional metrics may be calculated for each row, such as the standard deviation of pixel values.

In operation 410, an offset gain curve is calculated. This may be done by subtracting the target representative pixel value from the image intensity curve. The target representative pixel value may be a predetermined constant. The target representative pixel value may be selected through testing. Alternatively, the target representative pixel value may be selectable or adjustable by the user.

In operation 412, the offset time-gain curve is combined with the current time-gain curve to yield a corrected time-gain curve. This may be done, for example, by adding all or a fraction of the offset time-gain curve to the current time-gain curve.

In operation 414, the corrected gain curve is smoothed. Various smoothing techniques may be used such as a linear curve fit or a polynomial fit. In one embodiment, a quadratic polynomial fit is used to smooth the corrected time-gain curve.

In operation 416, the smoothed time-gain curve is temporally smoothed to ease the transition. In one embodiment an infinite impulse response filter (IIR) is used to transition to the new gain curve In any of the above embodiments it can be convenient to define a reference level and to represent pixel values relative to the reference level. In some embodiments pixel values are represented in decibels (dB) relative to the reference level.

FIGS. 5A-5J illustrate various steps of example method 400 of the present disclosure.

FIG. 5A is an example grayscale ultrasound image. The ultrasound image has been log-compressed so that each pixel is represented by a value between 0 and 255. The image may or may not have had image enhancement applied.

FIG. 5B depicts the grayscale ultrasound image of FIG. 5A that has been divided into a number of rectangular regions. In this example, the image has been divided into 5 columns and 10 rows of regions. The number of columns and rows of regions may be different in different embodiments. In some embodiments the number of rows and/or columns is adjusted adaptively based on settings for ultrasound acquisition unit 102. For example the number of rows of regions may increase as the depth of ultrasound imaging is increased and/or as the frequency of ultrasound energy transmitted is increased.

FIG. 5C is an example matrix of the average pixel values of each region

FIG. 5D is an example matrix of the average pixel value of each region transformed into decibels. This transformation is dependent on the dynamic range of the pixel values and the noise floor. In the example embodiment the transformation involved the computation:

$$\text{Gain (dB)} = \text{Pixel Intensity}/255 * \text{Dynamic Range (dB)} + \text{Noise Floor (dB)}.$$

In this example, the noise floor was 8 dB and dynamic range was 60 dB. The deadband was defined by a threshold of 3 dB. A target gain of 24 dB was desired. The applied gain varied linearly from 15 dB to 33 dB.

FIG. 5E depicts an example matrix where the average pixel intensities are masked based on a minimum threshold. In this case, the threshold is 11 dB, which removes a region from the leftmost column.

FIG. 5F depicts an example of the averaged row intensities, the target gain, and the applied gain. In this example, the horizontal axis represents gain in decibels while the vertical axis represents depth in millimeters. The average of each row intensity is represented by an open circle and connected with a thick line for clarity. The gain applied to generate the current image is shown as a thin solid line. The target gain is shown as a dashed line. In the example, the target gain is 24 dB.

FIG. 5G depicts an example corrected time-gain curve illustrated by open diamonds connected by a thick solid line. This curve is an example of the type of curve produced by operations 410 and 412 described above.

FIG. 5H is an example of a corrected target time-gain curve, a quadratic curve fit, a lower and upper boundary curves, and a smoothed target time-gain curve. The quadratic curve, shown as a dashed line, is fit to the corrected time-gain curve shown in FIG. 5G. The upper and lower bounds, shown as dash-dot lines, are generated by applying a clipping offset to the quadratic fit. The smoothed target time-gain curve, shown as a thick line, is produced by restricting the corrected time-gain curve to fall between the boundaries.

Figure 5I:
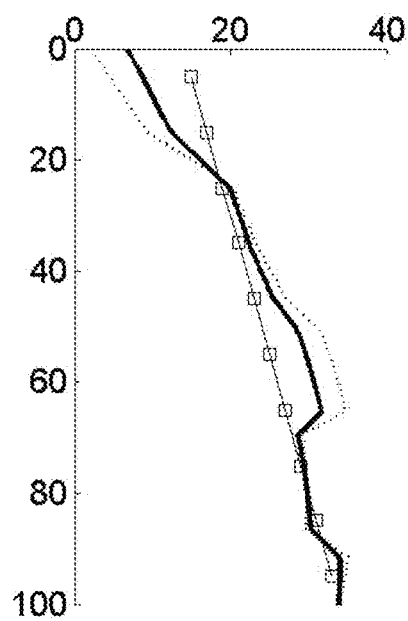
FIG. 5I is an example transition gain curve.

FIG. 5I depicts an example of a smoothed gain curve, a current gain curve, and a transition time-gain curve. The smoothed gain curve, shown as a dotted line, is combined with the current gain curve, shown as series of squares connected by thin line, to produce the transition gain curve, shown as a thick line.

Figure 5J:
FIG. 5J is an example offset grayscale ultrasound image with an updated gain curve.

FIG. 5J depicts an example ultrasound image with an updated time-gain curve applied.

Figure 6:
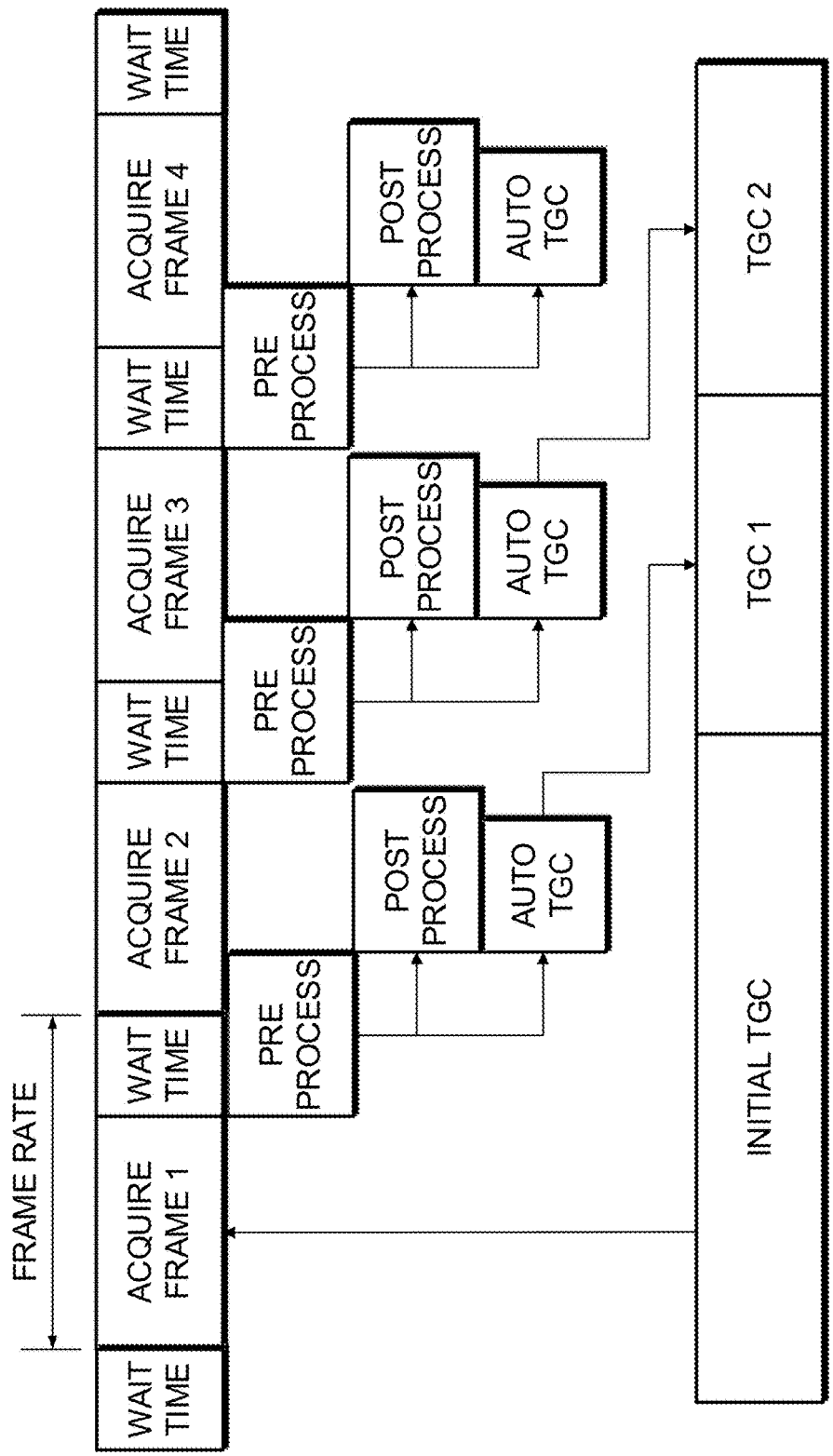
FIG. 6 is a timing diagram of an example embodiment of the present disclosure.

FIG. 6 is an example timing diagram according to one or more embodiments of the present disclosure. When the system is first initialized, an initial predetermined TGC curve stored in memory or in a script is selected based on the imaging preset and loaded into ultrasound acquisition unit 102. A first frame is acquired using the initial TGC curve. Once the initial pre-processing produces a log-compressed image, the AutoTGC unit and the post-processing unit operate in parallel. The updated time-gain curve from the first frame is stored in memory and loaded into the receiver before the third frame is acquired.

The second frame is also acquired using the initial TGC curve while the first frame is being processed. The gain calculation for the second frame includes the result from the first gain analysis.

In other embodiments, the automatic TGC unit may not analyze every frame. For example, gain may be analyzed every Nth frame where N is a suitable integer (e.g. if N=10 every $10^{th}$ frame). This analysis frequency may be a predetermined constant or may be variable. In the case of a predetermined constant, the analysis frequency may be selected and defined with a particular imaging preset. Alternatively, the analysis frequency may be variable. The analysis frequency may be adjustable by the user in real-time or as a setting. The analysis frequency may be adjusted to find a balance between performance and power saving. The analysis frequency could also be adjusted automatically. For example, the analysis frequency may be increased in cases where probe motion is detected or large changes in the image are detected. This may increase performance by more quickly adapting to different imaging situations that result when the probe is move to a new location, for example. This may also allow for conserving power when minimal changes are detected and it is not necessary to change the gain as frequently.

Example Operation

The following describes an example of how the system may be used.

An operator turns on apparatus as described herein and selects an imaging preset suitable for an ultrasound examination to be conducted. The imaging preset is associated with a number of parameters that are loaded into the device memory. These parameters may include noise floor, dynamic range, an initial gain curve, a desired gain level, vertical and horizontal region number, dead zone threshold, transition speed and others. The initial gain curve is loaded into memory.

When the operator starts imaging, the ultrasound controller sends the initial gain curve to the analog front end to apply the correct gain at the appropriate time in the receive cycle. This initial data is then processed in a way familiar to those with ordinary skill in the art into a log-compressed image.

The autogain unit receives the log-compressed image and calculates the appropriate update gain as a function of time based on the image, the desired gain level, the initial gain curve and the parameters associated with the current imaging preset. If the updated time-gain differs from the current time-gain by more than the dead zone threshold, the updated time-gain curve is supplied to the analog front end where the updated time-gain curve is used for a subsequent acquisition receive cycle. Otherwise, the previous time-gain curve is reused.

When a large change in gain settings are required, for example, when the operator first places the probe in contact with the patient, the gain will quickly and smoothly be transitioned over several acquisition cycles depending on the transition speed without requiring intervention from the operator.

In an embodiment with variable transition speed, the transition speed may be increased when a large change in probe orientation or position is detected to quickly transition to a more appropriate gain curve. The transition speed may be decreased once probe movement is stabilized in order to reduce stabilize the image and reduce flickering and unnecessary changes. Probe orientation or changes in probe position may be detected using appropriate sensors (e.g. accelerometers or electromagnetic or optical or acoustic position sensors) and/or by performing analysis of received ultrasound images.

While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like.

For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Certain aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, some aspects of the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging method comprising:
acquiring ultrasound data by transmitting ultrasound signals and receiving ultrasound echo signals using a probe, and amplifying the ultrasound echo signals according to gains that vary with echo delay times according to a current time-gain curve;
processing the ultrasound data to yield an ultrasound image;
determining a time-gain compensation curve by:
   determining a representative pixel value for each of a plurality of regions of the ultrasound image, wherein each region comprises a plurality of pixels values, and wherein the regions are arranged in a plurality of rows with each row comprising a plurality of the regions, and wherein each row corresponds to an echo delay time on the current time-gain curve;
   for each row of regions, combining those of the representative pixel values which satisfy an inclusion condition into a combined representative pixel value associated with the row;
   for the combined representative pixel values of each row, determining a gain offset amount by which to correct the gain of the current time-gain curve at that row, the gain offset amount being the difference between the combined representative pixel value for the row and a target gain;
   based on the gain offset amounts, adjusting the time-gain curve to generate a corrected time-gain curve;
repeating the acquiring ultrasound data, the processing the ultrasound data to yield an ultrasound image, and the determining a time-gain compensation curve for a plurality of temporally spaced-apart frames, wherein the determining the time-gain compensation curve further comprises:
   processing the corrected time-gain curve through a temporal filter; and
   monitoring motions of the probe, and controlling the temporal filter to have a higher time constant when the probe is moving less and controlling the temporal filter to have a lower time constant when the probe is moving more.

2. A method according to claim 1 wherein the representative pixel values comprise average pixel values.

3. A method according to claim 1 wherein the inclusion condition comprises the representative pixel value exceeding a threshold.

4. A method according to claim 1 comprising spatially smoothing the corrected time-gain curve to yield a target time-gain curve.

5. A method according to claim 4 wherein spatially smoothing the corrected time-gain curve comprises fitting a function to the corrected time-gain curve.

6. A method according to claim 5 wherein the function is a linear or a polynomial function.

7. A method according to claim 5 comprising determining measures of the distributions of different pixel values within some or all of the regions and the fitting of the function is based on the measures of the distributions.

8. A method according to claim 7 wherein the measures of the distributions comprise standard deviation.

9. A method according to claim 1 wherein the temporal filter comprises an infinite impulse response filter.

10. A method according to claim 1 wherein the regions are arranged to provide at least four rows with at least three regions in the four rows.

11. A method according to claim 10 comprising automatically changing a number of rows of the regions based on a setting of an ultrasound depth control.

12. A method according to claim 1 wherein each of the regions has a height of 2 or more rows of the ultrasound image and a width of at least 2 columns of the ultrasound image.

13. A method according to claim 1 comprising when all of the gain offset amounts are within a deadzone, suppressing adjusting the time-gain curve.

14. A method according to claim 1, wherein one or more ultrasound frames is acquired between two consecutive frames of the plurality of temporally spaced-apart frames.

15. An ultrasound imaging system comprising:
an ultrasound data acquisition unit for acquiring ultrasound data by transmitting ultrasound signals and receiving ultrasound echo signals;
a plurality of variable gain amplifiers connected to amplify the ultrasound echo signals according to gains that vary with echo delay times according to a current time-gain curve;
a beamformer connected to process the ultrasound data to yield an ultrasound image; and,
a processor configured by instructions in a memory operatively coupled to the processor to determine a time-gain compensation curve, wherein, when the instructions are executed, the processor is configured to:
determine a representative pixel value for each of a plurality of regions of the ultrasound image, wherein each region comprises a plurality of pixel values, and wherein the regions are arranged in a plurality of rows with each row comprising a plurality of the regions, and wherein each row corresponds to an echo delay time on the current time-gain curve;
for each row of regions, combine those of the representative pixel values which satisfy an inclusion condition into a combined representative pixel value associated with the row;
for the combined representative pixel values of each row, determine a gain offset amount by which to correct the gain of the current time-gain curve at that row, the gain offset amount being the difference between the combined representative pixel value for the row and a target gain;
based on the gain offset amounts, adjust the time-gain curve to generate a corrected time-gain curve;
wherein the acquiring ultrasound data, the processing the ultrasound data to yield an ultrasound image, and the determining a time-gain compensation curve is repeated for a plurality of temporally spaced-apart frames, and wherein to determine the time-gain compensation curve, the instructions further configure the processor to:
process the corrected time-gain curve through a temporal filter; and
monitor motions of the probe, and control the temporal filter to have a higher time constant when the probe is moving less and control the temporal filter to have a lower time constant when the probe is moving more.

\* \* \* \* \*